United States Patent
Peglion et al.

[11] Patent Number: 5,958,927
[45] Date of Patent: Sep. 28, 1999

[54] INDANOL COMPOUNDS

[75] Inventors: Jean-Louis Peglion, Le Vesinet; Bertrand Goument, Viroflay; Mark Millan; Adrian Newman-Tancredi, both of Le Pecq; Anne Dekeyne, Saint Remy les Chevreuses, all of France

[73] Assignee: Adir et Compagnie, Courbevoie, France

[21] Appl. No.: 09/165,844

[22] Filed: Oct. 2, 1998

[30] Foreign Application Priority Data

Oct. 3, 1997 [FR] France ................................ 97 12336

[51] Int. Cl.⁶ .................. A61K 31/495; C07D 405/10; C07D 409/10; C07D 411/10
[52] U.S. Cl. .................. 514/254; 544/376; 544/377; 546/197; 546/196; 546/202; 546/280.1; 546/282.1; 546/282.4; 546/282.7; 546/281.7; 546/283.1; 546/280.4; 546/280.7; 546/281.1; 514/320; 514/321; 514/324; 514/337; 514/338
[58] Field of Search ................... 544/376, 377; 514/254

[56] References Cited

U.S. PATENT DOCUMENTS 4,782,061  11/1988  Kruse et al. .......................... 514/254
5,194,437  3/1993  Peglion .................................. 514/254
5,753,662  5/1998  Peglion et al. ....................... 514/254

FOREIGN PATENT DOCUMENTS

87/02035  4/1987  WIPO .

Primary Examiner—Mukund J. Shah
Assistant Examiner—Ann Kessinger
Attorney, Agent, or Firm—The Firm of Gordon W. Hueschen

[57] ABSTRACT

A compound of formula (I):

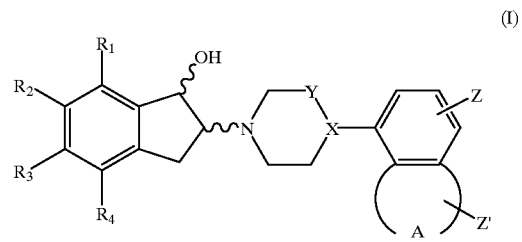

wherein $R_1$, $R_2$, $R_3$, $R_4$, X-Y, A, Z and Z' are as defined in the description, in the form of the cis or trans isomers each in racemic or optically active form, and acid addition salts thereof, and medicinal products containing the same are useful in the treatment of diseases of the central nervous system or of manifestations of pain.

14 Claims, No Drawings

INDANOL COMPOUNDS

FIELD OF THE INVENTION

The present invention relates to new indanol compounds. The compounds of the present invention find advantageous therapeutic use in the treatment of diseases of the central nervous system or of manifestations of pain.

DESCRIPTION OF THE PRIOR ART

A large number of serotonin receptor sub-types have been identified hitherto. Within the $5\text{-}HT_1$ receptor class itself, molecular biology studies and pharmacological studies have enabled sub-division to be made between five different receptors, $5\text{-}HT_{1A}$, $5\text{-}HT_{1B}$, $5\text{-}HT_{1D}$, $5\text{-}HT_{1E}$, $5\text{-}HT_{1F}$, (Humphrey, P. P. A. et al., A proposed new nomenclature for 5-HT receptors, *Trends in Pharmacological Sciences*, 1993, 14, 233).

Previous studies carried out in the Applicant's laboratories (U.S. Pat. No. 5,194,437) had made it possible to show that compounds of the type:

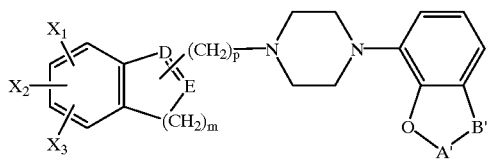

had $5\text{-}HT_{1A}$ serotoninergic receptor antagonist properties.

Research carried out since then in the Applicant's laboratories has enabled the identification of substances that differ structurally from the preceding substances by the presence of an alcohol function on the pentagonal ring of the indane group, which makes the new compounds much safer to use owing to the better receptor selectivity of the compounds of the invention. It has in fact been possible to increase the ratio between the $5\text{-}HT_{1A}$ and $\alpha_1$ affinities on the one hand and the $5\text{-}HT_{1A}$ and $D_2$ affinities on the other hand by minimising the effects at the $\alpha_1$ and $D_2$ sites. The new compounds thus behave like much more selective $5\text{-}HT_{1A}$ ligands and consequently induce fewer side-effects. The prior art can also be illustrated by Patent WO 87/02035 which claims cyclic amino alcohols of general formula:

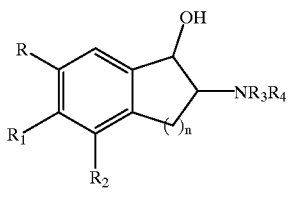

wherein $NR_3R_4$ may be:

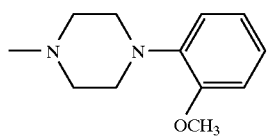

However, those compounds are used in the treatment of cardiovascular diseases (antihypertensives, platelet anti-aggregants, spasmolytics, etc.) and could not have inspired the compounds of the present invention nor their use in the areas claimed hereinafter.

In vivo studies carried out with the compounds of the present invention have confirmed the results obtained in vitro in the binding studies and have identified the site of action, since the $5HT_{1A}$ receptors are located both at the pre-synaptic and post-synaptic levels.

Indeed, recording of the unitary extracellular electrical activity in the dorsal nucleus of the raphe in rats makes it possible to determine the $5\text{-}HT_{1A}$ agonist or antagonist character at the pre-synaptic level, whilst the body temperature test in rats makes it possible to demonstrate the post-synaptic agonist or antagonist character of the compounds of the invention. Finally, the ultrasonic vocalisation test in rats is effective in providing information on the anxiolytic effects of the products tested.

Accordingly, it will be possible to use the compounds of the present invention advantageously in diseases of the central nervous system, especially anxiety, depression, psychoses, schizophrenia, cognitive disorders, stress and anorexia, and in the treatment of manifestations of pain.

DETAIL DESCRIPTION OF THE INVENTION

More specifically, the present invention relates to the indanol compounds of formula (I):

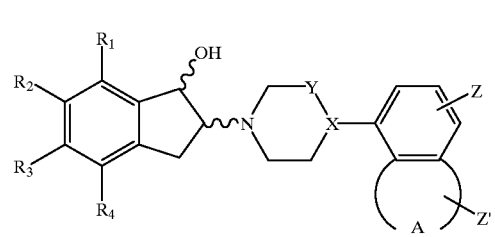

wherein:

$R_1$, $R_2$, $R_3$ and $R_4$, which may be identical or different, each represent a hydrogen or halogen atom, a $(C_1\text{-}C_5)$ alkyl, $(C_2\text{-}C_5)$alkenyl or $(C_2\text{-}C_5)$alkynyl radical, those radicals being linear or branched chain, a cycloalkylalkyl radical in which the cycloalkyl moiety contains from 3 to 7 carbon atoms and the alkyl moiety contains from 1 to 5 carbon atoms, a trifluoromethyl, CHO, COOH, $COO(C_1\text{-}C_5)$alkyl, $CO(C_1\text{-}C_5)$alkyl, $CH_2OH$, hydroxy, $(C_1\text{-}C_5)$-alkoxy, $(C_2\text{-}C_5)$alkenoxy, $(C_2\text{-}C_5)$ alkynoxy, benzyloxy, cyano, nitro radical,

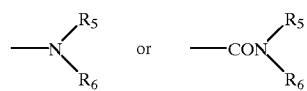

wherein $R_5$ and $R_6$, which may be identical or different, each represent a hydrogen atom or a $(C_1\text{-}C_5)$alkyl, $\text{---}CO(C_1\text{-}C_5)$ alkyl or $\text{---}COO(C_1\text{-}C_5)$alkyl radical; or $R_1$, $R_2$, $R_3$ and $R_4$, taken in pairs in adjacent positions, form with the carbon atoms of the phenyl nucleus to which they are bonded a 5- to 7-membered ring, containing one or more double bonds and composed of atoms selected from carbon, oxygen, nitrogen and sulphur atoms, and others radical, being not taken in pairs in adjacent positions, each represent a hydrogen atom, X-Y represents:

N—CH$_2$, C═CH, CH—CH$_2$ or

A forms with the two carbon atoms of the phenyl ring to which it is bonded a 5- to 7-membered heterocycle containing one or more double bonds and comprising one or two hetero atoms, which may be identical or different, selected from oxygen and sulphur atoms;

Z represents a hydrogen or halogen atom or a hydroxy or (C$_1$–C$_5$)alkoxy radical, and Z' represents a hydrogen atom or an oxo, hydroxy, (C$_1$–C$_5$)alkoxy or CH$_2$OH radical, in the form of the cis or trans isomers, it being possible for each of those to exist in racemic or optically active form, and addition salts thereof with a pharmaceutically acceptable acid.

Accordingly, in formula (I), the

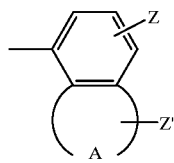

group represents more specifically:

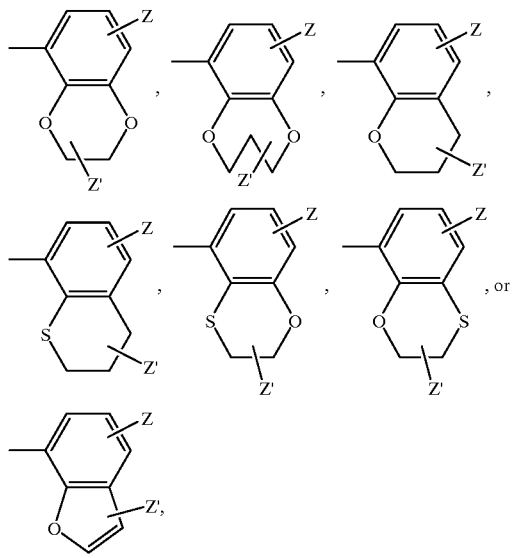

wherein Z and Z' are as defined hereinbefore.

The invention also extends to a process for the preparation of compounds of formula I characterised in that a ketone of formula II:

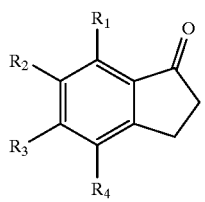

wherein R$_1$, R$_2$, R$_3$ and R$_4$ are as defined hereinbefore, is halogenated in the α position of the ketone function to obtain a compound of formula III:

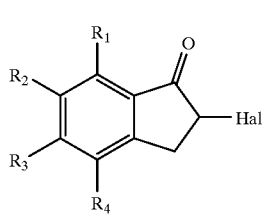

wherein R$_1$, R$_2$, R$_3$ and R$_4$ are as defined hereinbefore and Hal represents a chlorine, bromine or iodine atom, which compound III is reacted with an amine of formula IV:

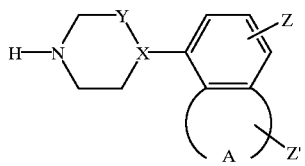

wherein X-Y, A, Z and Z' are as defined hereinbefore, to yield a compound of formula V:

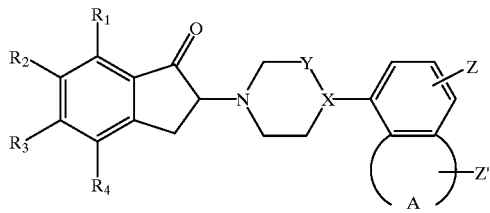

wherein R$_1$, R$_2$, R$_3$, R$_4$, X-Y, A, Z and Z' are as defined hereinbefore, which is reduced to a mixture of amino alcohols of formulae I trans and I cis:

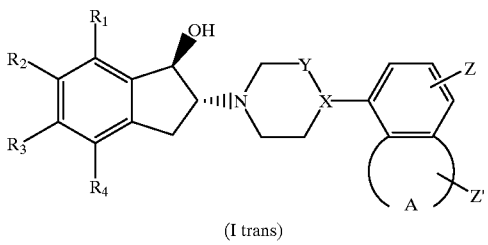

(I trans)

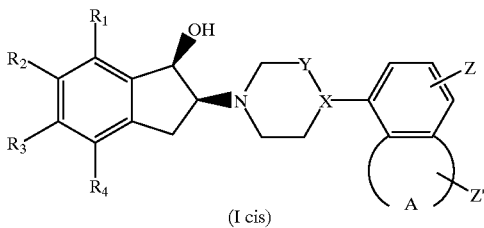

(I cis)

wherein $R_1$, $R_2$, $R_3$, $R_4$, X-Y, A, Z and Z' are as defined hereinbefore.

The compounds I trans and I cis are then separated by conventional methods for separating organic compounds, that is to say by fractional recrystallisation, separation over a silica column (flash chromatography) or separation by H.P.L.C. (High Performance Liquid Chromatography).

The totality of the compounds I trans and I cis constitutes the totality of the compounds of formula I.

Compounds of formula I wherein X-Y represents C=CH or CH—$CH_2$, that is to say compounds corresponding more specifically to formula Ia:

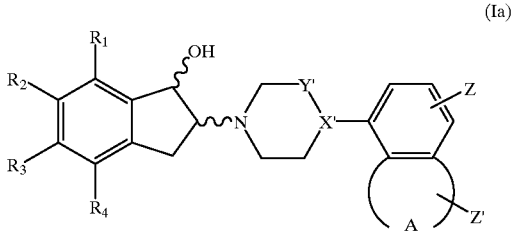

(Ia)

wherein:

$R_1$, $R_2$, $R_3$, $R_4$, A, Z and Z' are as defined hereinbefore and
X'-Y' represents C=CH or CH—$CH_2$, may also be prepared advantageously using the following method characterised in that a compound of formula VI:

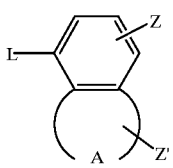

(VI)

wherein:

A, Z and Z' are as defined hereinbefore, and
L represents a labile group selected from Br, I and $OSO_2CF_3$, is reacted with diethyl(pyrid-1-yl)borane under the conditions of the Suzuki reaction, to obtain a compound of formula VII:

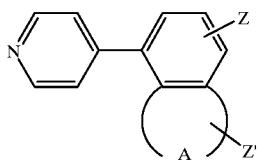

(VII)

wherein A, Z and Z' are as defined hereinbefore, which is reacted with a compound of formula III defined hereinbefore, to obtain a compound of formula VIII:

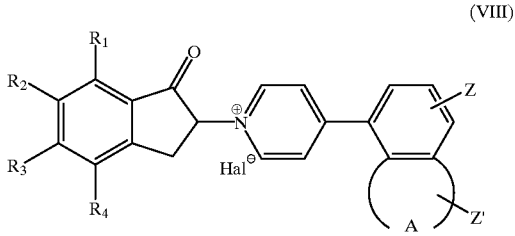

(VIII)

wherein $R_1$, $R_2$, $R_3$, $R_4$, A, Z, Z' and Hal are as defined hereinbefore, which is reduced with a metal borohydride in an alcoholic solvent to yield a mixture of amino alcohols of formulae I'a trans and I'a cis:

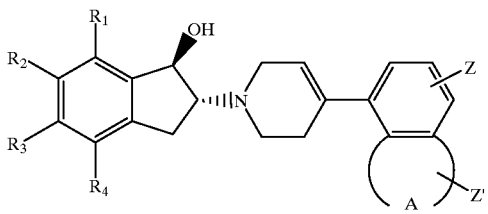

(I'a trans)

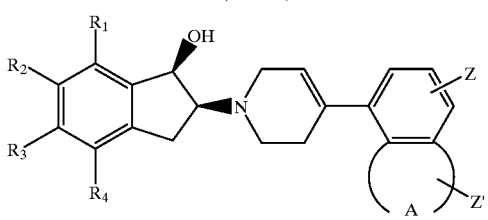

(I'a cis)

wherein $R_1$, $R_2$, $R_3$, $R_4$, A, Z and Z' are as defined hereinbefore, which amino alcohols are, if desired, reduced again, with hydrogen in the presence of a suitable catalyst, to compounds of formulae I"a trans and I"a cis:

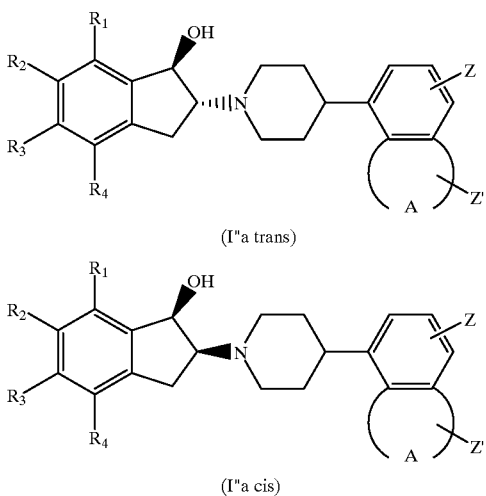

wherein $R_1$, $R_2$, $R_3$, $R_4$, A, Z and Z' are as defined hereinbefore, and, when Z' represents an oxo radical, it is advantageous to start from a compound VII in which the oxo function is protected, for example in the form of 1,3-dioxolane, and then deprotected at the level of the compounds I'a trans and I'a cis or at the level of the compounds I"a trans and I"a cis, the compounds I'a trans and I'a cis on the one hand and the compounds I"a trans and I"a cis on the other hand are then separated by conventional methods for separating organic compounds, that is to say by fractional recrystallisation, separation over a silica column or separation by H.P.L.C.

The totality of the compounds I'a trans, I'a cis, I"a trans and I"a cis constitutes the totality of the compounds of formula Ia, which is included in formula I.

The halogenation of compound II is a standard reaction which can be carried out using a large number of reagents. When the halogen atom is a bromine atom, the reaction can be carried out advantageously using tetrabutylammonium tribromide in methanol and methylene chloride.

The reaction of compound III with compound IV is carried out, inter alia, advantageously in dimethylformamide in the presence of $K_2CO_3$.

The starting materials of formula II and of formula VI, when they are not commercial products, were prepared starting from known substances, in accordance with processes described in the literature.

The optically active forms of the compounds of formula I were obtained by separating the racemic forms of the compounds of formula I or analogues thereof esterified at the alcohol function of the indanol, in accordance with methods known in the literature.

The present invention relates also to pharmaceutical compositions containing as active ingredient at least one compound of formula I or a physiologically tolerable salt thereof, mixed or in association with one or more suitable pharmaceutical excipients.

The resulting pharmaceutical compositions are generally presented in unit dose form containing from 0.5 to 25 mg of active ingredient. For example, they may be in the form of tablets, dragees, gelatin capsules, suppositories, injectable or drinkable solutions, and may be administered orally, rectally or parenterally.

The dosage may vary according to the age and weight of the patient, the route of administration, the nature of the disease and associated treatments, and ranges from 0.5 to 25 mg of active ingredient, from 1 to 3 times per day.

The following examples, which are given by way of non-limiting example, illustrate the present invention. The melting points were determined either using a Kofler hot plate (K) or a hot plate under a microscope (MK).

EXAMPLE 1

Cis-2-[4-(2,3-dihydro[1,4]benzodioxin-5-yl) piperazin-1-yl]-6-methoxyindan-1-ol

Step 1: 2-Bromo-6-methoxyindan-1-one 49.2 g (102 mmol) of tetra-n-butylammonium tribromide are added in fractions over the course of 15 minutes, at room temperature, to 16.2 g (100 mmol) of 6-methoxy-indan-1-one dissolved in 400 ml of methanol and 1 liter of dichloromethane, and the mixture is then stirred overnight at room temperature. After evaporation, the residue is taken up in 500 ml of dichloromethane and washed twice with 250 ml of N hydrochloric acid. Drying over magnesium sulphate and concentration, and then rapid filtration over 500 g of silica (eluant: dichloromethane) yield 23.4 g of the desired product.

Yield: 97%

Step 2: 2-[4-(2,3-Dihydro[1,4]benzodioxin-5-yl) piperazin-1-yl]-6-methoxy-indan-1-one A suspension prepared from 25.3 g (100 mmol) of the compound obtained in Step 1, 22.0 g (100 mmol) of (2,3-dihydro[1,4]benzodioxin-5-yl)piperazine, 13.8 g (100 mmol) of potassium carbonate and 140 ml of dimethylformamide is stirred at room temperature for 20 hours. The mixture is then poured into 1.5 liters of water, and the solid that forms (violet) is filtered off, rinsed with water and dried in vacuo to obtain 28.1 g of the expected product.

Yield: 74%

Step 3: Title compound 2.8 g (73.8 mmol) of sodium borohydride are added in fractions over the course of 15 minutes at room temperature to 28.0 g (73.6 mmol) of the compound obtained in Step 2 in 220 ml of tetrahydrofuran. The mixture is stirred overnight at room temperature, and then for 4 hours at reflux. After evaporation, the residue is taken up in 1 liter of dichloromethane, washed twice with 500 ml of water and then dried over magnesium sulphate. After concentration, the residue is chromatographed over silica (eluant: dichloromethane/methanol 99/1, then 98/2). The product eluted first corresponds to the cis isomer. Its stereochemistry was demonstrated by IR, in solution in chloroform, according to the method described by H. -J. Rimek et al. (*Justus Liebigs Ann. Chem.*, 1969, 726, 25–29).

IR(CHCl$_3$): $\nu_{OH\ bonded}$: 3380 cm$^{-1}$(broad band)

m.p.(MK): 207–210° C.

EXAMPLE 2

Trans-2-[4-(2,3-dihydro[1,4]benzodioxin-5-yl) piperazin-1-yl]-6-methoxyindan-1-ol The product eluted second in the chromatography carried out in Step 3 of the preceding sExample corresponds to the title compound. Its stereochemistry was demonstrated according to the same method as above.

IR(CHCl$_3$): $\nu_{OH\ free}$: 3580 cm$^{-1}$(narrow band)

m.p.(MK): 145–148° C.

EXAMPLE 3

Cis-2-[4-(2,3-dihydro[1,4]benzodioxin-5-yl) piperazin-1-yl]-5-methoxyindan-1-ol

Prepared in the same manner as the compound of Example 1, but using 5-methoxyindan-1-one instead of 6-methoxyindan-1-one in Step 1.

IR(CHCl$_3$): $\nu_{OH\ bonded}$: 3400 cm$^{-1}$(broad band)
m.p.(MK): 214–217° C.

EXAMPLE 4

Trans-2-[4-(2,3-dihydro[1,4]benzodioxin-5-yl)piperazin-1-yl]-5-methoxyindan-1-ol Prepared in the same manner as the compound of Example 2, but using 5-methoxyindan-1-one instead of 6-methoxyindan-1-one in Step 1 of Example 1.

IR(CHCl$_3$): $\nu_{OH\ free}$: 3700 cm$^{-1}$ and 3600 cm$^{-1}$(narrow bands)
m.p.(MK): 137–140° C.

EXAMPLE 5

Cis-2-[4-(2,3-dihydro[1,4]benzodioxin-5-yl)piperazin-1-yl]indan-1-ol

Prepared in the same manner as the compound of Example 1, but using indan-1-one instead of 6-methoxyindan-1-one in Step 1.

IR(CHCl$_3$): $\nu_{OH\ bonded}$: 3400 cm$^{-1}$(broad band)
m.p.(MK): 196–198° C.

EXAMPLE 6

Trans-2-[4-(2,3-dihydro[1,4]benzodioxin-5-yl)piperazin-1-yl]indan-1-ol

Prepared in the same manner as the compound of Example 2, but using indan-1-one instead of 6-methoxyindan-1-one in Step 1 of Example 1.

IR(CHCl$_3$): $\nu_{OH\ free}$: 3600 cm$^{-1}$(narrow band)
m.p.(MK): 211–214° C.

EXAMPLE 7

(+)-Trans-2-[4-(2,3-dihydro[1,4]benzodioxin-5-yl)piperazin-1-yl]indan-1-ol

Step 1: (±)-Trans-1-(1-acetoxyindan-2-yl)-4-(2,3-dihydro[1,4]benzodioxin-5-yl-piperazine 4.9 g of the compound obtained in Example 6 are treated at room temperature overnight with 706 ml of acetic anhydride and 141 ml of pyridine. After concentration of the reaction mixture, the concentrate is take up in water and methylene chloride. After decanting, the organic phase is washed, dried, evaporated and purified by chromatography over a silica column to yield 5.2 g of expected product.

Step 2: Separation of the optical isomers

The 5.2 g of product obtained in the preceding Step are separated by H.P.L.C., over a chiral phase. An eluant prepared from an isooctane/ethanol/diethylamine mixture makes it possible to isolate 1.8 g of a pure compound that corresponds to the first peak; the pure second isomer (1.1 g) corresponding to the second peak is obtained using an eluant composed of an n-heptane/ethanol/diethylamine mixture.

Step 3: Title compound

The 1.8 g of the first product obtained in the chromatographic separation of Step 2 are treated with 1.28 g of potassium hydroxide, 18 ml of water and 160 ml of methanol, at reflux for 2 hours. Concentration is carried out and the concentrate is taken up in methylene chloride, washed with water, dried and evaporated to yield, after recrystallisation of the residue, 0.44 g of a product that melts at 184–186° C. (MK) and corresponds to the expected structure in an enantiomeric excess of 99%.

$[\alpha]^{20°\ C.}$ (c=0.5% in CH$_3$OH):

| λ nm | 589 | 578 | 546 | 436 | 365 |
|---|---|---|---|---|---|
| α° | +22.1 | +22.9 | +26.1 | +47.2 | +79.6 |

EXAMPLE 8

(−)-Trans-2-[4-(2,3-dihydro[1,4]benzodioxin-5-yl)piperazin-1-yl]indan-1-ol

The 1.1 g of the second product obtained in the chromatographic separation are treated in the same manner as in the course of Step 3 of Example 7 to yield 0.27 g of a product that melts at 186–189° C. (MK) and corresponds to the expected structure in an enantiomeric excess of more than 97%.

$[\alpha]^{20°\ C.}$ (c=0.5% in CH$_3$OH):

| λ nm | 589 | 578 | 546 | 436 | 365 |
|---|---|---|---|---|---|
| α° | −20.9 | −22.1 | −25.4 | −45.7 | −77.1 |

EXAMPLE 9

Cis-2-[4-(2,3-dihydro[1,4]benzodioxin-5-yl)piperazin-1-yl]-6-hydroxyindan-1-ol 0.77 g of the compound of Example 1 is suspended at −20° C. in methylene chloride. 4.1 ml of a boron tribromide solution (1M in methylene chloride) are added dropwise thereto. The mixture is stirred for 3 hours at −20° C. and is then allowed to return to room temperature and is subsequently left for 3 days with stirring. The resulting precipitate is filtered off and washed with methylene chloride. It is solidified from water to yield 0.58 g of a product which corresponds to the hydrobromide of the expected product. Freeing of the salt by a sodium hydrogen carbonate solution, extraction with methylene chloride, evaporation and solidification yield 0.25 g of the expected product.

The compounds of the following Examples were prepared from the corresponding starting materials by proceeding as in Example 1:

EXAMPLE 10

Cis-2-[4-(2,3-dihydro[1,4]benzodioxin-5-yl)piperazin-1-yl]-5-fluoroindan-1-ol m.p. (MK)=210–213° C.

EXAMPLE 11

Cis-2-[4-(2,3-dihydro[1,4]benzodioxin-5-yl)piperid-1-yl]-5-fluoroindan-1-ol m.p. (MK)=197–201° C.

EXAMPLE 12

Cis-2-[4-(3,4-dihydro-2H-chromen-8-yl)piperazin-1-yl]-5-fluoroindan-1-ol m.p.(MK)=209–210° C.

EXAMPLES 13 TO 16

The compounds of the following Examples were prepared from the corresponding starting materials in the same manner as the compound of Example 2:

EXAMPLE 13

Trans-2-[4-(2,3-dihydro[1,4]benzodioxin-5-yl)
piperazin-1-yl]-5-fluoroindan-1-ol m.p. (MK)=220–224° C.

EXAMPLE 14

Trans-2-[4-(2,3-dihydro[1,4]benzodioxin-5-yl)
piperid-1-yl]-5-fluoroindan-1-ol m.p. (MK)=204–209° C.

EXAMPLE 15

Trans-2-[4-(3,4-dihydro-2H-chromen-8-yl)piperazin-
1-yl]-5-fluoroindan-1-ol m.p. (MK)=148–150° C.

EXAMPLE 16

Trans-2-{4-[2,3-dihydro-2-(hydroxymethyl)[1,4]-
benzodioxin-5-yl]piperazin-1-yl}-6-methoxyindan-1-ol

EXAMPLE 17

Trans-2-{4-[7-chloro-2,3-dihydro-2-
(hydroxymethyl)[1,4]-benzodioxin-5-yl]piperazin-1
-yl}-5-fluoroindan-1-ol

EXAMPLE 18

Cis-2-[4-(2,3-dihydro [1,4]benzodioxin-5-yl)-1,2,3,
6-tetrahydropyrid-1-yl]indan-1-ol Step 1: 4-(2,3-Dihydro[1,4]benzodioxin-5-yl)pyridine 14.7 mmol of diethyl(pyrid-4-yl)borane, 22 mmol of 5-bromo-2,3-dihydro[1,4]-benzodioxine, 44.1 mol of KOH in powder form, 7.4 mmol of tetrabutylammonium bromide and 0.74 mmol of tetrakis(triphenylphosphine)palladium in 75 ml of tetrahydrofuran are mixed at room temperature, and the mixture is then refluxed for 24 hours. 225 ml of ethyl acetate are added and the mixture is washed with a saturated sodium chloride solution. Drying is carried out over $MgSO_4$, followed by evaporation and purification over a silica column (eluant $CH_2Cl_2$, then $CH_2Cl_2/CH_3COOC_2H_5$ 80/20).

Yield: 52%

Step 2: 4-(2,3-Dihydro[1,4]benzodioxin-5-yl)-1-(indan-1-one-2-yl)-pyridinium bromide 2.41 g of the compound obtained in the preceding Step and 2.45 g of 2-bromo-indan-1-one are dissolved in 35 ml of acetone and refluxed for 24 hours. After cooling, the solid is filtered off, rinsed with acetone and dried in vacuo to yield 2.7 g of product which corresponds to the expected structure.

Step 3: Title compound 1.18 g of sodium borohydride are added in fractions over the course of 30 minutes at room temperature to 2.6 g of the compound obtained in the preceding Step suspended in 50 ml of methanol (very strongly exothermic) and the mixture is then stirred at room temperature for 30 minutes. 2.8 ml of acetic acid are then added and evaporation to dryness is carried out. The residue is taken up in 50 ml of N sodium hydroxide solution and extracted twice with 50 ml of methylene chloride. The organic phases are washed with water, dried, evaporated and chromatographed over silica, eluant $CH_2Cl_2/CH_3COOC_2H_5$ 90/10, then $CH_2Cl_2/CH_3OH$ 99/1. The first product eluted is recrystallised from ethanol to yield 0.27 g of expected product.

m.p. (MK)=109–112° C.

The cis stereochemistry of the product is demonstrated by infrared, in solution in chloroform, according to the method described by H. J. Rimek et al. (Justus Liebigs Ann. Chem., 1969, 726, 25–20).

IR(CHCl$_3$): $v_{OH\ bonded}$: 3400 cm$^{-1}$(broad band)

EXAMPLE 19

Trans-2-[4-(2,3-dihydro[1,4]benzodioxin-5-yl)-1,2,3,
6-tetrahydropyrid-1-yl]indan-1-ol The product eluted second in the chromatography carried out in Step 3 of the preceding Example corresponds to the title compound.

m.p. (MK)=182–184° C.

Its stereochemistry was demonstrated according to the method used in the preceding Example.

IR(CHCl$_3$): $v_{OH\ free}$: 3600 cm$^{-1}$(narrow band)

EXAMPLE 20

Trans-2-[4-(2,3-dihydro[1,4]benzodioxin-5-yl)-1,2,3,
6-tetrahydropyrid-1-yl-5-fluoroindan-1-ol Prepared using, in succession, the methods described in Examples 18 and 19, but using 2-bromo-5-fluoroindan-1-one instead of 2-bromoindan-1-one in Step 2 of Example 18.

The melting point (MK) of the title compound is 198–202° C.

EXAMPLE 21

Trans-2-[4-(3,4-dihydro-2H-thiochromen-8-yl)-1,2,
3,6-tetrahydropyrid-1-yl]-5-fluoroindan-1-ol Prepared using, in succession, the methods described in Examples 18 and 19, but using 3,4-dihydro-2H-thiochromen-8-yl triflate instead of 5-bromo-2,3-dihydro[1,4]-benzodioxine in Step 1 of Example 18, and using 2-bromo-5-fluoro-indan-1-one instead of 2-bromo-indan-1-one in Step 2 of Example 18.

The melting point (MK) of the title compound is 143–147° C.

EXAMPLE 22

Trans-2-[4-(3,4-dihydro-2H-chromen-8-yl)-1,2,3,6-
tetrahydropyrid-1-yl]-5-fluoroindan-1-ol Prepared using, in succession, the methods described in Examples 18 and 19, but using 8-bromo-3,4-dihydro-2H-chromene in Step 1 of Example 18, and using 2-bromo-5-fluoro-indan-1-one in Step 2 of Example 18.

EXAMPLE 23

Trans-2-[4-(2,3-dihydro[1,4]benzodioxin-5-yl)
piperid-1-yl]indan-1-ol 0.44 g of the compound obtained in Example 19 dissolved in 20 ml of $CH_3OH$ is hydrogenated at room temperature and atmospheric pressure in the presence of platinum oxide. Purification over a silica column and recrystallisation from acetonitrile yield 0.17 g of a product, the structure of which corresponds to that of the expected product.

m.p. (MK)=173–174° C.

EXAMPLE 24

Trans-2-[4-(benzofuran-7-yl)piperid-1-yl]-5-
fluoroindan-1-ol

Prepared using, in succession, the methods described in Examples 18, 19 and 23, but using 7-bromobenzofuran instead of 5-bromo-2,3-dihydro[1,4]benzodioxine in Step 1 of Example 18, and using 2-bromo-5-fluoroindan-1-one instead of 2-bromo-indan-1-one in Step 2 of Example 18.

The melting point (MK) of the title compound is 170–172° C.

EXAMPLE 25

Trans-2-[4-(2,3-dihydro[1,4]benzodioxin-5-yl)piperid-1-yl]-6-fluoroindan-1-ol

Prepared using, in succession, the methods described in Examples 18, 19 and 23, but using 2-bromo-6-fluoro-indan-1-one instead of 2-bromo-indan-1-one in Step 2 of Example 18.

The melting point (MK) of the title compound is 159–163° C.

EXAMPLE 26

Trans-2-[4-(2,3-dihydro[1,4]benzodioxin-5-yl)piperid-1-yl]-5-methylindan-1-ol

Prepared using, in succession, the methods described in Examples 18, 19 and 23, but using 2-bromo-5-methyl-indan-1-one in Step 2 of Example 18.

The melting point (MK) of the title compound is 191–192° C.

EXAMPLE 27

Trans-2-[4-(2,3-dihydro[1,4]benzodioxin-5-yl)piperid-1-yl]6-methylindan-1-ol

Prepared using, in succession, the methods described in Examples 18, 19 and 23, but using 2-bromo-6-methylindan-1-one in Step 2 of Example 18.

The melting point (MK) of the title compound is 225–226° C.

EXAMPLE 28

Trans-2-[4-(2,3-dihydro[1,4]benzodioxin-5-yl)piperid-1-yl]-5,6-difluoroindan-1-ol Prepared using, in succession, the methods described in Examples 18, 19 and 23, but using 2-bromo-5,6-difluoroindan-1-one in Step 2 of Example 18.

The melting point (MK) of the title compound is 167–169° C.

EXAMPLE 29

Trans-2-[4-(3,4-dihydro-6-fluoro-2H-chromen-8-yl)piperid-1-yl]-5-fluoroindan-1-ol Prepared using, in succession, the methods described in Examples 18, 19 and 23, but using 3,4-dihydro-2H-6-fluorochromen-8-yl triflate instead of 5-bromo-2,3-dihydro[1,4]-benzodioxine in Step 1 of Example 18, and using 2-bromo-5-fluoroindan-1-one instead of 2-bromoindan-1-one in Step 2 of Example 18.

The melting point (MK) of the title compound is 160–162° C.

EXAMPLE 30

Trans-2-[4-(2,3-dihydro[1,4]benzodioxin-5-yl)piperid-1-yl]-5,6-methylenedioxyindan-1-ol Prepared using, in succession, the methods described in Examples 18, 19 and 23, but using 2-bromo-5,6-methylenedioxyindan-1-one in Step 2 of Example 18.

The melting point (MK) of the title compound is 212–215° C.

EXAMPLE 31

Trans-2-[4-(2,3-dihydrobenzofuran-7-yl)piperid-1-yl]-5-fluoroindan-1-ol

Prepared using, in succession, the methods described in Examples 18, 19 and 23, but using 7-bromo-2,3-dihydrobenzofuran in Step 1 of Example 18, and using 2-bromo-5-fluoro-indan-1-one in Step 2 of Example 18.

The melting point (MK) of the title compound is 215–217° C.

EXAMPLE 32

Trans-2-[4-(2,3-dihydro [1,4]benzodioxin-5-yl)-4-hydroxypiperid-1-yl]-5-fluoroindan-1-ol Prepared using, in succession, the methods described in Examples 1 and 2, but using 5-fluoroindan-1-one in Step 1 of Example 1, and using 4-(2,3-dihydro[1,4]benzodioxin-5-yl)-4-hydroxypiperidine in Step 2 of Example 1.

EXAMPLES 33 to 42

The compounds of the following Examples were prepared from the corresponding starting materials by proceeding as described in Examples 24 to 31:

EXAMPLE 33

Trans-2-[4-(7-chloro-2,3-dihydro[1,4]benzodioxin-5-yl)piperid-1-yl]-5-fluoroindan-1-ol m.p. (MK)=175–177° C.

EXAMPLE 34

Trans-2-[4-(3,4-dihydro-2H-chromen-8-yl)piperid-1-yl]-5-fluoroindan-1-ol

EXAMPLE 35

Trans-6-bromo-2-[4-(3,4-dihydrobenzodioxin-5-yl)piperid-1-yl]indan-1-ol

EXAMPLE 36

Trans-6-cyano-2-[4-(2,3-dihydro[1,4]benzodioxin-5-yl)piperid-1-yl]indan-1-ol

EXAMPLE 37

Trans-6-carbamoyl-2-[4-(2,3-dihydro[1,4]benzodioxin-5-yl)piperid-1-yl]indan-1-ol

EXAMPLE 38

Trans-2-[4-(2,3-dihydro[1,4]benzodioxin-5-yl)piperid-1-yl]-6-trifluoromethylindan-1-ol

EXAMPLE 39

Trans-2-[4-(3,4-dihydro[1,4]-2H-chromen-8-yl)piperid-1-yl]indan-1-ol

EXAMPLE 40

Trans-2-{4-[2,3-dihydro-2-(hydroxymethyl)[1,4]benzodioxin-5-yl]piperid-1-yl}-5-fluoroindan-1-ol

EXAMPLE 41

Trans-2-{4-(3,4-dihydro)-4-oxo-2H-chromen-8-yl] piperid-1-yl}-5-fluoroindan-1-ol, In this case additionally using the method of protecting/deprotecting the oxo function.

EXAMPLE 42

Trans-2-{4-[(3,4-dihydro)-4-hydroxy-2H-chromen-8-yl]piperid-1-yl}-5-fluoroindan-1-ol

EXAMPLE 43

Pharmacological Study

A. In vitro study

Determination of affinity for human h5-$HT_{1A}$ receptors

Affinity was determined by competition experiments with [$^3$H]-8-OH-DPAT (NEN, Les Ulis, France). The membranes prepared from CHO cells transfected with the human 5-$HT_{1A}$ receptor were prepared as described by Newman-Tancredi et al., (*Neuropharmacol*, 1997, 36, 451–459). The membranes are incubated in triplicate with 0.4 nM [$^3$H]-8-OH-DPAT and the cold ligand in a final volume of 1.0 ml for two and a half hours at 25° C. The incubation buffer contains 25 mM HEPES-NaOH(pH 7.4) and 5 mM $MgCl_2$. The non-specific binding is determined using 10 μM 5-HT. At the end of incubation, the incubation medium is filtered through WHATMAN GF/B filters that have been impregnated with 0.1% polyethylenimine and have been washed three times with 5 ml of cooled buffer. The radioactivity retained on the filters is determined by liquid scintillation counting. The binding isotherms are analysed by non-linear regression using 'PRISM' software (Graphpad Software Inc., S. Diego, USA) to determine the $IC_{50}$ values. These are converted into dissociation constants ($K_i$) by means of the Cheng-Prusoff equation:

$$K_i = IC_{50}/(1+L/K_d)$$

wherein L is the concentration of [$^3$H]-8-OH-DPAT and $K_d$ is the dissociation constant of [$^3$H]-8-OH-DPAT for the human h5-$HT_{1A}$ receptor (0.65 nM).

By way of Example and to illustrate the activity of the compounds of the invention, the compound of Example 6 has a $K_i$ of 1.73 nM.

Determination of affinity for $\alpha_1$ receptors of rats

Affinity was determined by competition experiments with [$^3$H]-prazosin (NEN, Les Ulis, France). The membranes are prepared from frontal cortex of rat as described by Millan et al. (*J. Pharmacol. Exp. Ther*, 1995, 275, 885–898). The membranes are incubated in triplicate with 0.2 nM [$^3$H]-8-OH-DPAT and the cold ligand in a final volume of 1.0 ml for 60 minutes at 25° C. The incubation buffer contains 50 nM TRIS-HCl (pH 7.4), 4 mM $CaCl_2$, 0.1% (w/v) of ascorbic acid and 10 μM pargyline. The non-specific binding is determined using 10 μM phentolamine. At the end of incubation, the incubation medium is filtered through WHATMAN GF/B filters that have been impregnated with 0.1% polyethylenimine and have been washed three times with 5 ml of cooled buffer. The radioactivity retained on the filters is determined by liquid scintillation counting. The binding isotherms are analysed by non-linear regression using 'PRISM' software (GraphPad Software Inc., S. Diego, USA) to determine $IC_{50}$ values. These are converted into dissociation constants ($K_i$) by means of the Cheng-Prusoff equation:

$$K_i = IC_{50}/(1+L/K_d)$$

wherein L is the concentration of [$^3$H]-prazosin and $K_d$ is the dissociation constant of [$^3$H]-prazosin for the $\alpha_1$ receptor (0.1 nM).

By way of Example and to illustrate the activity of the compounds of the invention, the compound of Example 6 has a $K_i$ of 932 nM.

These two results illustrate well the excellent selectivity of the compounds of the invention for the 5-$HT_{1A}$ receptor compared with that for the $\alpha_1$ receptor, which should result in products having no cardiovascular side-effects and that are accordingly safer to use.

B. In vivo study

1. "In vivo" recording of unitary extracellular electrical activity in the dorsal nucleus of the raphe in rats (pre-synaptic 5-$HT_{1A}$ receptors)

Principle

The administration of a 5-$HT_{1A}$ serotoninergic agonist decreases the discharge frequency of neurons in a dose-dependant manner. That effect is reversed by the selective 5-$HT_{1A}$ antagonist, WAY 100,635.

Method

The rats are anaesthetised with chloral hydrate (400 mg/kg, i.p.) and placed in a stereotaxis apparatus (Unimécanique, France) after catheterisation of the femoral vein. The level of anaesthesia is maintained by i.p. administration of chloral hydrate every hour; the rectal temperature is maintained at 37±1° C. by means of a thermostatically controlled heated cover. A tungsten microelectrode (10 MΩ, 1 μM) is inserted using an electronic microinsertion device (Unimécanique, France) into the dorsal nucleus of the raphe (AP: −7.8 bregma; L : 0.0; H: 5.0–6.5 dura; Paxinos and Watson Atlas, 1986). The potentials of the serotoninergic cells are characterised by their morphology (positive/negative biphase potentials, of a duration of less than 2.5 msec) and their slow and regular discharge rhythm of from 0.5 to 2.5 Hz. A single cell per animal is recorded.

After a period of ≧5 min (basal activity) and a first injection of carrier (distilled water to which a few drops of dilute lactic acid have been added, pH adjusted to 5 with 1N NaOH), the compound of the invention is administered intravenously in cumulatively increasing doses at intervals of 5 minutes.

Analysis of the results

Acquisition of the data is effected by the software Spike2 (Cambridge Electronic Design, England). The discharge frequency is measured over one minute at the maximum variation between each injection and is expressed as a percentage variation in relation to the basal activity (average of the 5 minutes preceding the first treatment) defined as 100%. The $ID_{50}$ is calculated using a simple linear regression method with repeated measurements.

Results

By way of Example, the following Table shows the effects of the compound of Example 6.

| Doses μg/kg i. v. | 0 | 0.25 | 0.5 | 1 | WAY 100, 365 31 μg/kg |
|---|---|---|---|---|---|
| Example 6 | 98.11 ± 2.21 | 73.84 ± 14.14 | 52.23 ± 19.38 | 36.16 ± 2.52 | 140.48 ± 20.11 |

Individual values (n = 3). Mean ± standard error of the mean.

The $ID_{50}$ of the compound of Example 6 in this test is 0.59 μg/kg when the product is administered intravenously. The result shows that the site of action, in vivo, of the compounds of the invention is indeed located at the level of the 5-$HT_{1A}$ receptors, as has already been shown in vitro, and that the compound of Example 6 behaves like a 5-$HT_{1A}$ serotoninergic agonist at the pre-synaptic level.

2. Body temperature test in rats (post-synaptic 5-$HT_{1A}$ receptors)

Principle

The administration of a 5-$HT_{1A}$ serotoninergic agonist, such as, for example, 8-OH-DPAT, brings about a decrease in body temperature in a dose-dependent manner. That effect is reversed by 5-$HT_{1A}$ antagonists, as has been shown by M.

J. Millan (*J. Pharmacol. Exp. Ther.*, 1993, 264, 1346–1376). According to the protocol described by that author, compounds of the invention which when administered on their own bring about a decrease in body temperature will be identified as post-synaptic $5\text{-}HT_{1A}$ serotoninergic agonists. On the other hand, compounds of the invention that reverse the hypothermia induced by the prototypical $5\text{-}HT_{1A}$ agonist 8-OH-DPAT will be identified as post-synaptic $5\text{-}HT_{1A}$ antagonists.

Results

By way of Example and to illustrate the effects of the compounds of the invention, the compound of Example 6 reverses the effects of 8-OH-DPAT at an $ID_{50}$ of 1.3 mg/kg s.c. It thus behaves like a post-synaptic $5\text{-}HT_{1A}$ serotoninergic antagonist.

3. Ultrasonic vocalisation test in rats

Principle

When a rat is placed in an environment previously associated with an unpleasant experience (electric shocks to the paws), its anxiety is shown by the emission of inaudible cries (or ultrasonic vocalisations). The anxiolytic activity of a compound is demonstrated by a reduction in the duration of those vocalisations.

Apparatus

Standard cages (Coulbourn Instruments), placed in sound-absorbing ventilated boxes, are fitted with a floor composed of electrifiable metal bars (shock generator and scrambler Med Associates Inc) and with a microphone located in the centre of the ceiling. The ultrasonic noises are converted into an audible range (bat-detector Buitenbedrijf). The signals modified in that manner are filtered and then processed (RTS software, Engineering Design). The spectrograms obtained are recorded on DAT tapes.

Method

Male Wistar rats weighing 180–200 g on their arrival are placed in cages of four with free access to water and food from five days before the start of the study until the end of the study. The procedure employed is divided into three successive stages separated by 24 hours, called training, selection and test. During the training period, the animals are placed individually into cages where they receive six electric shocks (0.8 mA, 8 s) distributed randomly over a period of seven minutes. Selection comprises placing each animal in a cage for two minutes where it receives a single shock and putting it back in the cage thirty minutes later to record the ultrasonic vocalisations for a period of ten minutes; those animals in which the duration of the vocalisations is less than 90 seconds are excluded from the remainder of the experiment. The test phase proceeds in a similar manner to the selection stage, except that the compounds or the carrier are administered at the end of the two-minute period.

Results

By way of Example, the following Table shows the effects of the compound of Example 6 administered subcutaneously in a volume of 1 ml/kg.

| dose mg/kg s. c. | duration of the ultrasonic vocalisations (s) mean ± s. e. m. (n) Example 6 |
|---|---|
| 0 | 230 ± 17 (8) |
| 0.04 | 170 ± 62 (6) |
| 0.16 | 28 ± 14 (3) ** |
| 2.5 | 8 ± 8 (5) ** | s. e. m.: standard error of the mean
n: number of rats
comparison with carrier (Dunnett test): ** p < 0.01

At doses of 0.16 and 2.5 mg/kg, that compound brings about a reduction in the duration of the vocalisations, indicating its anxiolytic activity.

We claim:

1. An indanol compound selected from those of formula I:

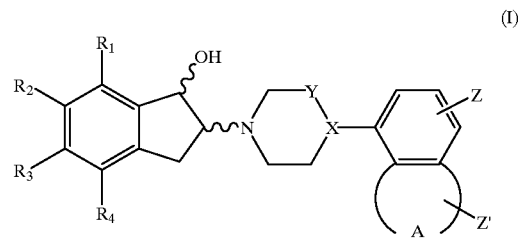

wherein:

$R_1$, $R_2$, $R_3$ and $R_4$, which may be identical or different, each represents hydrogen or halogen, $(C_1\text{-}C_5)$alkyl, $(C_2\text{-}C_5)$alkenyl, or $(C_2\text{-}C_5)$alkynyl, those radicals being linear or branched, cycloalkylalkyl in which cycloalkyl contains 3 to 7 carbon atoms inclusive and alkyl contains 1 to 5 carbon atoms, inclusive trifluoromethyl, CHO, COOH, $COO(C_1\text{-}C_5)$alkyl, $CO(C_1\text{-}C_5)$alkyl, $CH_2OH$, hydroxy, $(C_1\text{-}C_5)$-alkoxy, $(C_2\text{-}C_5)$alkenoxy, $(C_2\text{-}C_5)$alkynoxy, benzyloxy, cyano, nitro, or a group of formula:

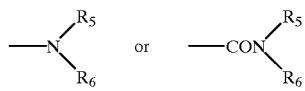

wherein $R_5$ and $R_6$, which may be identical or different, each represents hydrogen, halogen, $(C_1\text{-}C_5)$alkyl, $-CO(C_1\text{-}C_5)$alkyl, or $-COO(C_1\text{-}C_5)$alkyl, X-Y represents respectively:

$N-CH_2$,

A forms with the two carbon atoms of the phenyl ring to which it is bonded a 5- to 7-membered heterocycle containing one or more double bonds and comprising one or two heteroatoms, which may be identical or different, selected from oxygen and sulphur, Z represents hydrogen or halogen, hydroxy, or $(C_1\text{-}C_5)$ alkoxy, Z' represents hydrogen, oxo, hydroxy, $(C_1\text{-}C_5)$alkoxy, or $CH_2OH$, in the form of cis or trans isomers, each of those being in racemic or optically active form, and pharmaceutically-acceptable acid addition salts thereof.

2. A compound of claim 1 wherein:

$R_1$, $R_2$, $R_3$, $R_4$ and X-Y are as defined in claim 1 and the

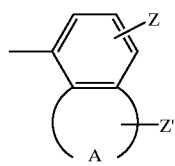

group represents more specifically:

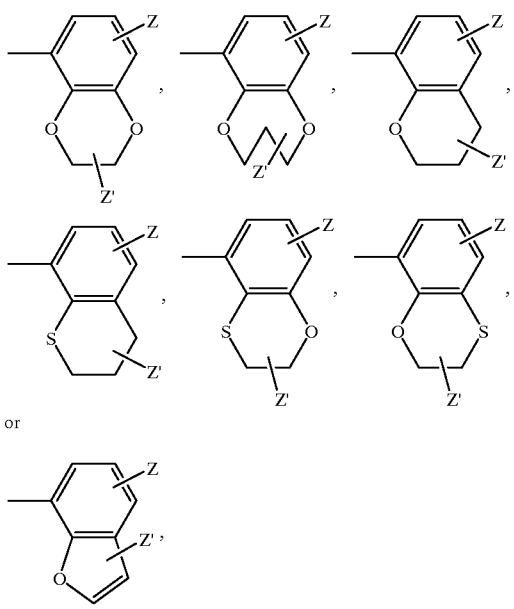

wherein Z and Z' are as defined in claim 1, in the form of cis or trans isomers, each of those being in racemic or optically active form, and pharmaceutically-acceptable acid addition salts thereof.

3. A compound of claim 1 which is trans-2-[4-(2,3-dihydro[1,4]benzodioxin-5-yl)piperazin-1-yl]-6-methoxyindan-1-ol.

4. A compound of claim 1 which is trans-2-[4-(2,3-dihydro[1,4]benzodioxin-5-yl)piperazin-1-yl]-5-methoxyindan-1-ol.

5. A compound of claim 1 which is trans-2-[4-(2,3-dihydro[1,4]benzodioxin-5-yl)piperazin-1-yl]indan-1-ol.

6. A compound of claim 1 which is (+)-trans-2-[4-(2,3-dihydro[1,4]benzodioxin-5-yl)piperazin-1-yl]indan-1-ol.

7. A compound of claim 1 which is (−)-trans-2-[4-(2,3-dihydro[1,4]benzodioxin-5-yl)piperazin-1-yl]indan-1-ol.

8. A compound of claim 1 which is trans-2-[4-(2,3-dihydro[1,4]benzodioxin-5-yl)piperazin-1-yl]-5-fluoroindan-1-ol.

9. A compound of claim 1 which is trans-2-[4-(3,4-dihydro-2H-chromen-8-yl)piperazin-1-yl]-5-fluoroindan-1-ol.

10. A compound of claim 1 which is trans-2-{4-[2,3-dihydro-2-(hydroxymethyl)[1,4]-benzodioxin-5-yl]piperazin-1-yl}-6-methoxyindan-1-ol.

11. A method for treating a living body afflicted with a condition selected from anxiety, depression, psychoses, schizophrenia, and pain, comprising the step of administering to the living body an amount of a compound of claim 1 which is effective for alleviation of said condition.

12. A pharmaceutical composition comprising as active principle an effective amount of a compound as claimed in claim 1, together with one or more pharmaceutically-acceptable excipients or vehicles.

13. A method for treating a living body afflicted with a condition selected from anxiety, depression, psychoses, schizophrenia, and pain, comprising the step of administering to the living body an amount of a compound of claim 2 which is effective for alleviation of said condition.

14. A pharmaceutical composition comprising as active principle an effective amount of a compound as claimed in claim 2, together with one or more pharmaceutically-acceptable excipients or vehicles.

* * * * *

UNITED STATES PATENT AND TRADEMARK OFFICE
CERTIFICATE OF CORRECTION

PATENT NO. : 5,958,927
DATED : Sep. 28, 1999
INVENTOR(S) : Jean-Louis Peglion, et al.

It is certified that error appears in the above-indentified patent and that said Letters Patent is hereby corrected as shown below:

Column 8, line 56: Delete the "s" before the word "Example". Page 10, line 17

Column 16, line 9: "synaptic $^5$-HT$_{1A}$" should read -- synaptic 5-HT$_{1A}$ --. Page 23, line 3

Column 16, line 48(approx.): "WAY 100,365" should read -- WAY 100,635 --. Page 24, line 10

Column 18, line 24: The "comma" after "atoms" should be moved to the end of -- inclusive --. Preliminary Amendment dtd 10-2-98, Claim 1, line 6.

Column 18, line 38: Insert the word -- or -- at the end of the line after "alkyl,". Page 27, line 14

Signed and Sealed this

Second Day of May, 2000

Attest:

Q. TODD DICKINSON

*Attesting Officer*         *Director of Patents and Trademarks*